(12) United States Patent
Bessette

(10) Patent No.: US 7,988,985 B2
(45) Date of Patent: Aug. 2, 2011

(54) PEST REPELLENT COMPOSITIONS AND METHODS

(75) Inventor: Steven M. Bessette, Brentwood, TN (US)

(73) Assignee: Ecosmart Technologies, Inc., Roswell, GA (US)

( * ) Notice: Subject to any disclaimer, the term of this patent is extended or adjusted under 35 U.S.C. 154(b) by 0 days.

(21) Appl. No.: 12/424,415

(22) Filed: Apr. 15, 2009

(65) Prior Publication Data

US 2009/0263515 A1   Oct. 22, 2009

Related U.S. Application Data

(60) Provisional application No. 61/045,941, filed on Apr. 17, 2008.

(51) Int. Cl.
*A01N 25/745* (2006.01)

(52) U.S. Cl. ........ 424/406; 424/405; 424/739; 424/745; 424/747; 424/DIG. 10; 514/739; 514/919

(58) Field of Classification Search .......................... None
See application file for complete search history.

(56) References Cited

U.S. PATENT DOCUMENTS

| 2002/0022043 A1* | 2/2002 | Miller ............................ 424/403 |
| 2002/0131986 A1* | 9/2002 | Clark et al. .................... 424/405 |
| 2003/0175369 A1* | 9/2003 | Khazan-Enache ............ 424/739 |
| 2003/0194454 A1* | 10/2003 | Bessette et al. ............... 424/745 |

FOREIGN PATENT DOCUMENTS

| DE | 5234383 | * | 6/1931 |
| WO | WO 99/52359 | * | 10/1999 |

\* cited by examiner

*Primary Examiner* — Neil Levy
(74) *Attorney, Agent, or Firm* — Nixon & Vanderhye P.C.

(57) ABSTRACT

The invention is directed to a topical insect repellent with extended duration of protection and that was obtained by combining natural and organic plant essential oil compounds. The new natural repellent exhibits the longevity and repellency that is comparable to or better than N,N-diethyl-m-toluamide (DEET), a synthetic compound employed in almost all commercial formulations, while at the same time is more acceptable than DEET, which has an unpleasant odor, imparts a greasy feel to the skin, and carries certain health concerns when used on children. The inventive insect repellent, formulated in a suitable carrier repels and incapacitates flying insects and other pests, such as mosquitoes and other biting flies or insects, thus demonstrating the utility of the novel insect repellent for protecting pets and livestock as well as humans. The invention provides an effective means to repel insects, without having deleterious effects on people, pets or the environment compared with prior insect repellant formulations. The repellant formulation disclosed herein may employ natural or organic active ingredient, e.g., plant essential oil compounds.

4 Claims, No Drawings

PEST REPELLENT COMPOSITIONS AND METHODS

CROSS REFERENCE TO RELATED APPLICATION

This application is related to and claims the benefit of U.S. Provisional Patent Application Ser. No. 61/045,941, filed Apr. 17, 2008, the entire disclosure of which is incorporated herein by reference.

FIELD OF THE INVENTION

The invention relates to pesticidal compositions for repelling pests, more specifically, insects and arthropods such as ticks, mites, mosquitoes, chiggers, punkies, noseeums, black flies, houseflies and other flying/biting insects, etc. (i.e., live approaching insects) using repellant effective compositions containing U.S. EPA exempt and/or biologically based organic active ingredients, which are safer for humans and other mammals, as described below.

BACKGROUND OF THE INVENTION

Repellents are substances having a repellent effect on insects or arthropods. Their use in human and veterinary hygiene is of great practical importance, where they protect man and beast against attack by bloodsucking, biting or otherwise annoying insects. It is required that repellents, which are directly applied onto the skin or fur, are well tolerated, non-toxic, perspiration-resistant and light-fast and perfect in cosmetic respects. Moreover, the protection of the treated areas should last for the longest possible period of time and the spectrum of activity should be as broad as possible, i.e. they should act against the largest possible number of harmful and annoying insects by repelling them.

In the past, essential oils such as citronella oil, camphor and eucalyptus oil have been used as natural repellents; however, due to their perceived disadvantages they were predominantly replaced by synthetic repellents, such as phthalic acid dimethyl ester, 1,2-ethyl hexane-1,3-diol, 3,4-dihydro-2,2-dimethyl-4-oxo-2H-pyran-6-carboxylic acid-n-butyl ester, succinic acid dipropyl ester, N,N-diethyl-3-methyl-benzoic acid amide, pyridine-2,5-dicarboxylic acid-d-n-propyl ester, etc. However, such synthetic repellents are often not perspiration-resistant and/or irritate the mucous membranes and skin and, more recently, some have been determined not to be bio-degradable.

Use of repellants is regulated in the United States by the Environmental Protection Agency (EPA) under authority of the Federal Insecticide, Fungicide and Rodenticide Act (FIFRA). To protect the public, the environment, and natural resources, repellants for all applications must be registered, unless they contain only ingredients that are specifically "exempt" from the registration requirements of the EPA. These exceptions or exemptions are updated from time to time and current lists may be obtained from the Environmental Protection Agency. Products containing exempted active ingredients and permitted inert ingredients are not required to satisfy the more rigorous registration requirements of FIFRA if contained on the above-mentioned lists. Such EPA exempt repellant products are highly desirable due to their safety profile and lack of persistence in the environment. Unfortunately, there is not guidance regarding how such listed ingredients may be used or combined to provide synergistic or even commercially economic effects.

Various insect pests, such as flying insects, including but not limited to arthropods (i.e. mosquitoes, noseeums), gnats and flies (house flies, black flies, horse flies, etc.), ticks and mites are a nuisance and may pose a health risk to humans, pets and other domesticated animals, particularly when the humans or animals are in outdoor environments. One attempt to reduce the nuisance and risk factors associated with such insect pests involves the use of various control or application means (e.g., topical repellants) for keeping various insect pests from flying or crawling near/on, stinging, biting, harming or otherwise annoying humans, pets and other domesticated animals. For instance, insect repellant compositions can be used in clothing, furniture, foodstuffs, or can be used nearby humans or animals, such as in candies or sprays to repel insect pests.

It is known that compositions derived from organic material, such as plant "essential oils" (e.g., oils produced from various plants & plant parts) have also been shown to have insect repellant and/or insecticide activity. Compounds isolated from plant essential oils as well as derivatives of these isolates have also been shown to have repellant or insecticidal activity. In today's market there are a number of plant essential oils being marketed to repel insects or animals. Plant essential oils tend to be volatile and will evaporate quickly when exposed to the elements. In many cases these essential oils are dissolved in mineral oil both to lower the cost and extend the useable life of the essential oil after it has been applied and exposed to the elements. The mineral oil acts as a carrier and a binder in this case and will greatly slow the evaporation of the essential oils. In addition, while many natural or organic based repellant compositions have been identified, highly effective compositions and formulations using such non-synthetic materials has not been known. Both synthetic or natural insecticides and insect repellants can be applied directly to a subject (i.e. topical application in creams, sprays or lotions), but may also be used with a variety of application systems (sprayers) to either kill or repel insects. Depending on the nature of the active ingredient, topical application may not be desirable as it can irritate the skin of the subject.

N,N,-diethyl-m-toluamide ("DEET") is the active ingredient found in most commercial topical insect repellents. The current U.S. Army insect repellent (EDTIAR) contains DEET as its active ingredient. DEET is a derivative of toluene, an organic solvent, and is regarded as a highly-effective biting-insect repellant yet discovered. How well DEET works depends on the concentration in which it's applied. Low-strength formulations containing 12.5% DEET are 60-75% effective. High-strength formulations containing up to 100% DEET can be 95%+effective for over 4 hours on blackflies (*Simulium* spp.) and up to 10-12 hours on mosquitoes (e.g., *Anopheles, Culex pipiens*, and *Aeges aegypti*). It is also somewhat effective in repelling ticks, chiggers, punkies, and noseeums. The major commercial brands, Off!®, Deep Woods Off!®, and Cutter®, are DEET based products and comprise a vast majority of insect repellent sales. Products with the highest concentration of DEET last the longest against mosquitoes, but excessive use of DEET is believed to pose some risk, especially for children. Other disadvantages associated with DEET include: it is a synthetic chemical having a limited spectrum of activity and a noticeably unpleasant odor; it is a powerful plasticizer and will dissolve or mar many plastics and painted surfaces; it plasticizes inert ingredients typically used in topical formulations in order to lengthen the time of effectiveness. As a result, DEET formulations have low user acceptability.

Desirable properties of a topical insect repellent include low toxicity, resistance to loss by water immersion or sweating, low or no odor or at least a pleasant odor, ease of application, and rapid formation of a dry tack-free surface film. Attempts to improve the properties of DEET through polymer or microcapsule formulation have been frustrated by DEET's plasticizing properties, which lead to a high tack skin surface. Further, efforts to develop a natural insect repellent have motivated studies of oils of citronella, turpentine, pennyroyal, cedarwood, eucalyptus and wintergreen, but these are relatively ineffective (see, e.g., *Handbook of Nonprescription Drugs*, 1993, 10th Ed., American Pharmaceutical Assn., Washington, D.C.). Some reports have indicated that "natural products" and products that do not contain DEET provided little or no protection against mosquitoes. Further, insect repellents for nonprescription oral use are not generally recognized as safe and effective (Federal Register, 1985, 50: 25170).

Clearly there is a need for a long-lasting effective insect and arthropod repellent that is pleasant to use and that will not damage plastic containers, or the text printed on the containers. Other desirable attributes include at least the following:

Formulations that contain no DEET
Safe around children and pets
Repel mosquitoes and ticks
Non-greasy and non-staining
Low odor
Works as well as or better than conventional DEET formulations

EXEMPLARY EMBODIMENTS

Various objects, features and attendant advantages of the invention will become more appreciated and understood from the explanations and examples set forth below, which are directed to repellant compositions and methods for repelling arthropods and flies, mosquitoes, noseeums, black flies, ticks, chiggers, houseflies and other crawling, flying, biting insects that approach humans and animals with repellant compositions containing non-DEET ingredients. The repellent according to the invention contains one or several substances prepared from harmless substances, and, consequently, possess the least toxicological and irritative risk with an excellent repelling effect. It is preferably used by applying it onto the skin of a mammal to repel approaching, flying, biting and/or sucking insects.

The current invention employs the use of specific plant essential oil mixtures and plant extracts that may have been listed in the EPA's "Generally Recognized as Safe" GRAS list for the purpose of repelling or otherwise discouraging arthropods (insects and arachnids) from inhabiting, crawling upon, or burrowing a treated surface. It will be appreciated by a skilled artisan that the repellant compositions of the invention exhibit excellent repellant activities by using one or more U.S. Food and Drug Administration approved plant essential oils that have been exempted from U.S. EPA registration, in lieu of conventional repellants that the above-described and other disadvantages. It will also be appreciated by the skilled artisan that the repellant compositions of the invention provide affordable repellant formulations and may be considered aesthetically acceptable for use on mammals. It will also be appreciated by the skilled artisan that the repellant compositions of the invention may unexpectedly exhibit excellent repellant activities compared to DEET formulations, and may, if desired, be formulated as water-based emulsions that form suspensions (such as emulsifiable concentrates, emulsions, or dispersions).

Utilizing the repellant compositions disclosed herein, the invention is directed to an inventive formulation for application to skin that has a natural pleasant feel, which is made from safe organic materials, and which is approximately as effective, or more effective, as DEET both in terms of repellency and duration of effect. The inventive formulation comprises a combination of two or more plant essential oils mixed in a dermatologically acceptable-carrier. The carrier allows the formulation to be adjusted to an effective concentration for repellancy. The carrier may further provide water repellency, prevent skin irritation, and/or soothe and condition skin. For example the carrier may include silicone, petrolatum, lanolin or any of several other well known carrier components.

The formulation of the invention may be a U.S. EPA exempt repellant formulation may comprise an active ingredient that has been shown to have repellant activity present in an amount of between about 0.1% to about 50% or more by weight/mass/volume and all subranges therebetween. The repellant liquid formulation may also comprise a fixative for reducing the vapor pressure of the active ingredient present in an amount of between about 0.2% to about 50% by weight/mass/volume and all subranges therebetween, an emulsifier present in an amount of between about 1% to 95% and all subranges therebetween, and/or a solvent liquid In an amount of between about 1% to 95% and all subranges therebetween. The active repellant ingredient may comprise a plant essential oil, an isolate of an essential oil, a derivative thereof, or a synthetic equivalent thereof, either alone or in combination. For example, the essential oils can include those oils described above, including certain isolates from the above noted oils, derivatives thereof, or the synthetic equivalent thereof.

Non-active ingredients (e.g., dermatologically-acceptable carriers) such as emulsifiers may include for example, silicone, polysorbate 20 and other similar grade emulsifiers of identical or generally similar hydrophobic-lypophobic balance and may be include mono-glyceride derivatives, polyoxyethylene nonyl phenolethers, and sugars esters and sodium lauryl sulfate (SLS), butyl lactate, isopropyl myristate or isopropyl alcohol (and analogs thereof); emulsifiers in the class polyoxyethylene condensation products with derivatives of sorbitol, lecithin of various origins such as soy and egg yolk. Further emulsifiers that may be employed include, without limitation, one of, or blends of two or more of: sorbitan monooleate; benzyl alcohol; tergitol; sodium alkyl ether sulfate; and the like.

Examples of insect repelling active ingredients that may be included in the repellant composition of the invention include, without limitation, rosemary, cinnamon, lemongrass, wintergreen, geraniol, canola oil, thyme, eugenol, peppermint, vanillin and/or sesame oil. Repellant formulations may contain a dermatologically-acceptable and/or inert carrier and an repellant active ingredient comprising at least one, two, three, four or more plant essential oil compounds, such as, without limitation, rosemary, cinnamon, lemongrass, wintergreen, geraniol, canola oil, thyme, eugenol, peppermint, vanillin and/or sesame oil. Two exemplary repellant formulations include, without limitation, the following (all stated concentrations below are approximate weight percent and include all subranges therebetween):

| Ingredient | Approximate Amount |
|---|---|
| Rosemary oil | about 0% to about 5% (and all subranges therebetween) |
| Cinnamon leaf oil | about 0% to about 5% (and all subranges therebetween) |
| Lemongrass oil | about 0% to about 5% (and all subranges therebetween) |
| Wintergreen oil | about 0% to about 5% (and all subranges therebetween) |
| Geraniol | about 0% to about 5% (and all subranges therebetween) |
| Canola oil | about 0% to about 5% (and all subranges therebetween) |
| Isopropyl Myristate (IPM) | about 0% to about 5% (and all subranges therebetween) |
| Isopropyl Alcohol (IPA) | about 0% to about 5% (and all subranges therebetween |

The invention is also directed to a method of repelling insects comprising applying to a mammal (human or animal) a repellant amount of the inventive repellant formulations described herein, i.e., onto the skin or fur of a human or animal.

By way of example, and not intending to be limited hereby, the invention will be further exemplified below. The following Examples are illustrative of various embodiments only and do not limit the claimed invention regarding the materials, conditions, weight ratios, process parameters and the like recited herein.

Example 1

The following are two exemplary non-limiting repellant formulations (all stated concentrations below are approximate weight percent):

| Ingredient | Composition DR-G-104 | Composition DR-G-079 |
|---|---|---|
| Rosemary oil | 0.5% | 0.5% |
| Cinnamon leaf oil | 0.5% | 0.5% |
| Lemongrass oil | 0.5% | 0.5% |
| Wintergreen oil | 0.5% | 0.5% |
| Geraniol | 1.0% | 1.0% |
| Canola oil | — | 5.0% |
| Isopropyl myristate (IPM) | 5.0% | 92.0% |
| Isopropyl alcohol (IPA) | 92.0% | — |

Example 2

Mosquito Spatial Repellency

Procedure: A static-air repellency chamber was used for determining the percentage (spatial) repellency of different EcoSmart repellant products denoted as DR-G-079 (a.k.a., Waterless Shoobug Lot E-2-26-183-1) and DR-G-104 (a.k.a., Waterless Shoobug Lot E-2-26-183-5). The apparatus used was a 9×60-cm section of glass tubing with a 2-cm center hole for introduction of the insects. Products were applied to 9-cm filter papers with either 2 or 3 pumps from a bottle. Treated filter papers were allowed to dry for 20 or 15 minutes, respectively. The position of the treated filter paper (right or left side of the chamber) was randomly assigned for each replication. Approximately 20 adult female yellow fever mosquitoes (*Aedes aegypti*) were anaesthetized with $CO_2$ and placed through the center hole via a funnel. Timing started after the mosquitoes recovered from $CO_2$. Observations were made up to 3 hours and treatments were replicated three times. Percentage repellency was calculated with the following formula:

[((individuals on untreated side−individuals on treated side)/total individuals)×100]

TABLE 1

Spatial repellency against female yellow fever mosquitoes (*Aedes aegypti*) with two pumps and 20 minutes to dry.

| | | Average Percentage Repellency | | | | | |
|---|---|---|---|---|---|---|---|
| Product | Lot | 15 min | 30 min | 60 min | 90 min | 120 min | 180 min |
| Waterless Shoobug | E-2-26-183-1 | 77 | 77 | 94 | 97 | 97 | 100 |
| Waterless Shoobug | E-2-26-183-5 | 97 | 97 | 97 | 100 | 100 | 100 |
| Control | | −12 | −8 | −8 | 2 | 8 | −3 |

TABLE 2

Spatial repellency against female yellow fever mosquitoes (*Aedes aegypti*) with three pumps and 15 minutes to dry.

| | | Average Percentage Repellency | | | | | |
|---|---|---|---|---|---|---|---|
| Product | Lot | 15 min | 30 min | 60 min | 90 min | 120 min | 180 min |
| Waterless Shoobug | E-2-26-183-1 | 63 | 81 | 85 | 88 | 94 | 90 |
| Waterless Shoobug | E-2-26-183-5 | 87 | 93 | † | † | † | † |
| Control | | −12 | −8 | −8 | 2 | 8 | −3 |

† > 70% of Individuals were knocked down at time point.

As the data shows, for DR-G-104 (a.k.a., Waterless Shoobug Lot E-2-26-183-5), two pumps from a bottle and a 20-minute drying period were efficacious. Products with IPA (DR-G-104 (a.k.a., Waterless Shoobug Lot E-2-26-183-5)) at three pumps still show efficacy. The DR-G-104 (a.k.a., Waterless Shoobug Lot E-2-26-183-5) demonstrated more repellency/quicker repellency than DR-G-079 (a.k.a., Waterless Shoobug Lot E-2-26-183-1).

Example 3

Mosquito-Spatial Repellency of DR-G-104 v. Off! Family

Procedure: A static-air repellency chamber was used for determining percentage (spatial) repellency of different EcoSmart products. The apparatus used was a 9×60-cm section of glass tubing with a 2-cm center hole for introduction of the insects. Products were applied to 9-cm filter papers with 2 pumps from a bottle of DR-G-104 (a.k.a., Waterless Shoobug Lot E-2-26-183-5) or Off! Family (with 7% DEET). Treated filter papers were allowed to dry for 20 minutes. The position of the treated filter paper (right or left side of the tube) was randomly assigned. Approximately 20 adult female yellow fever mosquitoes (*Aedes aegypti*) were anaesthetized with $CO_2$ and placed through the center hole via a funnel. Timing started after the mosquitoes recovered from $CO_2$. Observations were made up to 3 hours and treatments were replicated five times. Percentage repellency was calculated with the following formula:

[((individuals on untreated side−individuals on treated side)/total individuals)×100]

TABLE 1

Spatial repellency against female yellow fever mosquitoes (*Aedes aegypti*) with two pumps and 20 minutes to dry.

| | Average Percentage Repellency | | | | | |
|---|---|---|---|---|---|---|
| Product | 15 min | 30 min | 60 min | 90 min | 120 min | 180 min |
| Off Family (7% Deet) | 58 | 83 | 92 | 94 | 85 | 80 |
| Shoobug-E-2-26-183-5 | 70 | 75 | 88 | 86 | 83 | 79 |
| Control | 19 | 19 | 19 | 19 | 19 | 19 |
| Previous-E-2-26-183-5 | 97 | 97 | 97 | 100 | 100 | 100 |

The above data shows DR-G-104 (a.k.a., Waterless Shoobug Lot E-2-26-183-5), which contains no DEET performed as well as Off! Family with 7% DEET on *Aedes aegypti* in a static air chamber but with lower odor and less greasy feel.

Example 4

Mosquito *Culex pipiens*-Spatial Repellency

Procedure: A static-air repellency chamber was used for determining the percentage (spatial) repellency. The apparatus used was a 9×60-cm section of glass tubing with a 2-cm center hole for introduction of the insects. Products were applied to 9-cm filter papers with 2 pumps from a bottle of DR-G-104 (a.k.a., Waterless Shoobug Lot E-2-26-183-5) or Off! Family. Treated filter papers were allowed to dry for 20 minutes. The position of the treated filter paper (right or left side of the tube) was randomly assigned. Approximately 20 adult female northern house mosquito (*Culex pipiens*) were anaesthetized with $CO_2$ and placed through the center hole via a funnel. Timing started after the mosquitoes recovered from $CO_2$. Observations were made up to 3 hours and treatments were replicated five times. Percentage repellency was calculated with the following formula:

[((individuals on untreated side−individuals on treated side)/total individuals)×100]

TABLE 1

Spatial repellency against female northern house mosquito (*Culex pipiens*) with two pumps and 20 minutes to dry.

| | Average Percentage Repellency | | | | | |
|---|---|---|---|---|---|---|
| Product | 15 min | 30 min | 60 min | 90 min | 120 min | 180 min |
| Off Family (7% Deet) | 95 | 96 | 96 | 91 | 76 | 60 |
| Shoobug-E-2-26-183-5 | 92 | 98 | 98 | 100 | 98 | 76 |
| Control | 9 | 5 | 6 | −3 | 1 | 2 |
| Previous-E-2-26-183-5 | 97 | 97 | 97 | 100 | 100 | 100 |

The data shows that DR-G-104 (a.k.a., Waterless Shoobug Lot E-2-26-183-5), which contains no DEET performed as well as Off! Family with 7% DEET on *Culex pipiens* in the static air chamber but with lower odor and less greasy feel.

Example 5

Evaluation of the Repellency of Inventive Formulations to Family Off! Repellent Products Applied to Blood Membranes and Exposed to *Aedes aegypti* Mosquitoes Objectives: To determine the efficacy of multiple formulations of Waterless Shoobug (DR-G-079 (Shoobug #1) and DR-G-104 (Shoobug #2)) and the Off! Family mosquito repellent products applied to blood membranes and exposed to *Aedes aegypti* Mosquitoes under standard laboratory conditions whereby bite rates of the hematophagic arthropods (approximately 15 adult females) to on-body repellents with acrylic bite boxes attached to individually treated blood bladder membranes were measured in 3 replicates.

Treatments:
1. Untreated Controls
2. DR-G-079 ("Shoobug #1")
3. DR-G-104 ("Shoobug #2")
4. Family Off! (with 7% Deet)

Results/Discussion: The data is presented in Tables 1-4 below. Table 1 illustrates the average repellent performance of each test product at 1 hour after treatment. Table 2 illustrates the average repellent performance of each product tested at 2 hours after treatment. Table 3 illustrates the average repellent performance of the test products at 3 hours after treatment. For each replicate, 2 blood membranes were treated and exposed to a box of 15 unfed female mosquitoes. In each test, a product had 4 replicates, starting at the one hour interval, unless product failure (defined as two bites) occurred. Then the product would not move forward to be tested at a longer interval. This is illustrated in Table 2 with the OFF! Family product and in Table 3 with the ShooBug #2 product.

Table 4 illustrates a representative testing of industry standard product both with bite boxes on membranes and on human test subject to use as comparison. As can be seen at the 2, 3, and 4 hour intervals, the average number of bites on the treated arms is very similar to the average number of bites on the treated membrane system. This illustrates that the membrane system is an accurate simulation of the bite pressure and repellent degradation as on actual human arms.

The bite rates and first bite times were statistically compared with two t tests for independent samples. The first test was conducted using a one-tailed distribution and probability value of $p<0.05$ and is used to compared single treatment types to the untreated controls. The second was conducted using a two-tailed distribution and probability value of $p<0.05$ and is used to compared different treatments to one another.

At the 1 hour test interval, both ShooBug #1 and Shoobug #2 recorded one bite as a total number of bites as compared to OFF! Family which recorded 9 bites. During the 1 hour test, the bite pressure on the control replicates was recorded at 20 bites per box (avg). Of the tested products, OFF! Family demonstrated the earliest recorded bite at 0:49 seconds after exposure. The earliest recorded bites for ShooBug #1 and ShooBug #2 were obtained at 3:44 and 6:58 respectively. Statistically, all tested products demonstrated significant statistical differences between the treated replicates and the control replicates. There were no significant statistical differences between the ShooBug products. However, there was a significant statistical difference in performance between both ShooBug products and the OFF! Family product.

At the 2 hour test interval, only 1 one replicate of the OFF! Family product had not failed. ShooBug #1 and ShooBug #2 had all four replicates move forward in the testing. At this interval, ShooBug #1 recorded the first bite at 3:07 with an overall average of 6:18 for the four replicates. ShooBug #1 recorded a total of 9 bites for this interval. ShooBug #2 recorded the first bite at 0:47 with an overall average of 5:55 for the four replicates, with a total of 10 bites per replicate. OFF! Family recorded the first bite at 3:40 and a total of 9 bites. There were no significant statistical differences between the ShooBug products. However, there was a significant statistical difference in performance between both ShooBug products and the OFF! Family product.

Only one replicate of ShooBug #2 moved forward to the three hour interval. This replicate recorded the first bite at 1:59 and a total of 5 bites.

TABLE 1

Ave Efficacy of Products at 1 Hour After Application (4 Replicates per Product, 15 Adult Female Mosquitoes per Replicate)

| Treatment | Reps | Time of 1st Bite | Ave Time of 1st Bite | Total Bites | Ave Total Bites |
|---|---|---|---|---|---|
| control | 4 | 0:35 | 0:47 | 78 | 20 |
| ShooBug #1 | 5 | 3:44 | 2:03 | 1 | 0.25 |
| ShooBug #2 | 4 | 6:58 | 1:44 | 1 | 0.25 |
| OFF Family 7% | 4 | 0:49 | 5:23 | 9 | 2.25 |

TABLE 2

Ave Efficacy of Products at 2 Hours After Application (4 Replicates per Product, 15 Adult Female Mosquitoes per Replicate)

| Treatment | Reps | $1^{st}$ Bite | Ave $1^{st}$ Bite | Total Bites | Ave Bites |
|---|---|---|---|---|---|
| ShooBug #1 | 4 | 3:07 | 6:18 | 9 | 2.25 |
| ShooBug #2 | 4 | 0:47 | 5:55 | 10 | 2.5 |
| OFF Family (7%) | 1 | 3:40 | 3:40 | 9 | 9 |

TABLE 3

Ave Efficacy of Products at 3 Hours After Application (1 Replicate per Product, 15 Adult Female Mosquitoes per Replicate)

| Treatment | Reps | $1^{st}$ Bite | Ave $1^{st}$ Bite | Total Bites | Ave Bites |
|---|---|---|---|---|---|
| ShooBug #2 | 1 | 1:59 | 1:59 | 5 | 5 |

TABLE 4

Comparison Data (prior to EPA Restrictions) of Snell Sci Blood Membranes and Human (All products applied at the same rate/sq cm)
Comparison of Ave Efficacy of Deep Woods Off (w/25% DEET) When Applied to Arms of Human Tester vs Dual Membrane Bite Box in Repelling *Aedes aegypti* Mosquitoes at Varying Time Intervals After Application
15 Female Mosquitoes per Replicate

| | 2 hours | | | | 3 hours | | | | 4 hours | | | |
|---|---|---|---|---|---|---|---|---|---|---|---|---|
| Testing Surface | # of Reps | Ave time to $1^{st}$ Bite | Total Bites | Ave total bites per rep | # of Reps | Ave time of $1^{st}$ Bite | Total Bites | Ave total bites per rep | # of Reps | Ave time of $1^{st}$ Bite | Total Bites | Ave total bites per rep |
| Arms | 4 | 0:00 | 0 | 0 | 14 | 8:21 | 4 | 0:29 | 14 | 1:48 | 30 | 2:14 |
| Membranes | 6 | 4:37 | 1 | 0:17 | 32 | 1:28 | 37 | 1:17 | 30 | 0:47 | 59 | 1:96 |

Overall, at both the 1 hour and 2 hour intervals, both ShooBug products performed better than the OFF! Family product. Empirically, ShooBug #1 product had similar performance to the ShooBug #2 product at both the 1 hour and 2 hour testing intervals, but demonstrated a later first bite (3:07-vs-0:47) and a slightly lower average of total bites (2.25-vs-2.5) at the 2 hour interval. While statistically these 2 products are not different, it would seem that Shoobug #1 is slightly better than Shoobug #2.

Example 6

DR-G-104 v. OFF! Family (7% DEET) Against Deer Ticks (*Ixodes scapularis*) and the American Dog Tick (*Dermacentor variabilis*) In the Laboratory Repellency of DR-G-104 and Off! Family 7% DEET against *Ixodes scapularis* (Deer Tick)

DR-G-104 formulation of Shoobug (as previously described) and Off! Family (7% DEET) (purchased commercially) were tested for comparison using 15-cm plastic Petri dishes were used as the arena. Filter papers (12.5-cm diameter) were treated with product (100 μi) applied to a circular pencil line (2-inch diameter) in the center of the paper. One deer tick (*Ixodes scapularis*) was then placed into the center of the arena and allowed to move freely for 10 minutes (600 seconds). The product was applied with a pipette to the pencil line. The product did not always flow onto the paper in a smooth motion and thus made for an irregular band about 0.5 cm in width. Ticks were considered as not repelled if they crossed the pencil line by more than twice their body's length. This was due to the difficulty in applying the product evenly. Times were recorded up to 600 seconds or when they passed the line. Each product was replicated six times.

TABLE

|      | Control | Off Family | ShooBug |
|------|---------|------------|---------|
| Rep1 | 9       | 600        | 600     |
| Rep2 | 18      | 600        | 600     |
| Rep3 | 20      | 113        | 355     |
| Rep4 | 13      | 36         | 425     |
| Rep5 | 25      | 600        | 600     |
| Rep6 | 25      | 600        | 600     |
| Average | 18.3 | 424.8     | 530.0   |

Results

Average time to crawl out of the circle for the Control was 18.3 seconds, 425 seconds for Off! Family, and 530 seconds for DR-G-104.

Ticks were noticeably repelled, as indicated by walking up to the line and then turning around.

Both the Off! Family and DR-G-104 were statistically different from the control, but were not different from each other.

The Off! Family did have one extreme outlier (36 seconds).

Repellency of DR-G-104 and Off! Family 7% DEET Against *Dermacentor variabilis* (American Dog Tick)

A cotton wick, with a diameter of 1.25 cm was marked with a pencil line 2.5 cm from the bottom.

DR-G-104 formulation and Off! Family (7% DEET) (purchased commercially) were tested for comparison.

One milliliter of the product to be test and is applied in a 0.5-cm band above the line.

The glass container for the ticks is placed inside of a 15-cm2 plastic container filled with warm water to the brim (approximately 1.5 cm deep).

The cotton wick is then suspended down into the dish while the wick is attached to a clamp on a ring stand.

Four adult *Dermacentor variabilis* are placed into a glass container with an inside diameter of 3 cm and an outside diameter 3.8 cm, with an inside height of 1.3 cm.

Timing was started after all the replicates had four ticks placed into the container. Timing was for one hour.

Every ten minutes the ticks were blown on from over the top, looking down at the wick.

The number of ticks that crawled past the bottom line was recorded and used to calculate the percentage repellency.

Each product was replicated six times.

TABLE

|  | Control | | ShooBug | | Off Family | |
|---|---|---|---|---|---|---|
|  | # that climed (out of 4) | # passed line (out of 4) | # that climbed (out of 4) | # passed line (out of 4) | # that climbed (out of 4) | # passed line (out of 4) |
| Rep1 | 3 | 2 | 2 | 0 | 1 | 0 |
| Rep2 | 2 | 2 | 2 | 0 | 2 | 0 |
| Rep3 | 1 | 1 | 0 | 0 | 2 | 1 |
| Rep4 | 2 | 2 | 1 | 0 | 3 | 0 |
| Rep5 | 4 | 4 | 2 | 0 | 2 | 0 |
| Rep6 | 3 | 3 | 0 | 0 | 1 | 0 |
| Averages | 2.5 | 2.3 | 1.2 | 0.0 | 1.8 | 0.2 |
| Percentages | 63 | 58 | 29 | 0 | 46 | 4 |

Results

American dog ticks were likely to start climbing on the wick even with a treatment present; however, it was less likely that they would cross the treatment line.

Ticks, on average, climbed 63% of the time on the control (no product), 35% of the time with DR-G-104 applied, and 45% of the time with Off! Family applied. There may be a modest spatial repellency from the two treatments, since fewer ticks even tried to crawl Ticks, on average, were willing to pass the treatment line 58% of the time with the control, 0% of the time with DR-G-104 applied, and 4% of the time with Off! Family applied.

In addition to contact repellency, spatial repellency as well was observed, as well.

In summary, a novel insect and arthropod repellent that provides long lasting protection against at least mosquitoes and ticks, and that is stable, commercially available, economically competitive, safe for mammals, is described herein. The description of illustrative embodiments and best modes of the present invention are not intended to limit the scope of the invention. Although illustrative embodiments of the invention have been described in detail, it is to be understood that the invention is not limited to those precise embodiments, and that various changes and modifications can be effected therein by one skilled in the art without departing from the scope and spirit of the invention as defined herein. It is to be understood that each of the ranges recited above are intended to include all subranges therebetween.

What is claimed is:

1. A repellant composition comprising:
a carrier comprising isopropyl myristate in an amount of about 5.0% by weight and isopropyl alcohol in an amount of about 92% by weight; and
an active ingredient comprising rosemary oil in an amount of about 0.5% by weight, cinnamon leaf oil in an amount of about 0.5% by weight, lemongrass oil in an amount of about 0.5% by weight, wintergreen oil in an amount of about 0.5% by weight, and geraniol in an amount of about 1.0% by weight.

2. A method for repelling a pest selected from the group consisting of ticks, mites, mosquitoes, chiggers, punkies, noseeums, black flies and houseflies, the method comprising applying to a locus where pest repellency is desired, an effective amount of a pesticidally repellant composition comprising a carrier in an amount of from about 5.0% to about 92% by weight and comprising at least one member selected from the group consisting of isopropyl myristate and isopropyl alcohol and an active ingredient comprising rosemary oil in an amount of about 0.5% by weight, cinnamon leaf oil in an amount of about 0.5% by weight, lemongrass oil in an amount of about 0.5% by weight, wintergreen oil in an amount of about 0.5% by weight, and geraniol in an amount of about 1.0% by weight, with the proviso that no other pesticidally repellant ingredient is present.

3. The method of claim 2, wherein the locus is the skin or hair of a human mammal.

4. The method of claim 2, wherein the locus is the skin or hair of a non-human mammal.

* * * * *